(12) United States Patent
Banju et al.

(10) Patent No.: US 10,704,019 B2
(45) Date of Patent: Jul. 7, 2020

(54) CELL FILTRATION FILTER

(71) Applicant: Murata Manufacturing Co., Ltd., Nagaokakyo-shi, Kyoto-fu (JP)

(72) Inventors: Masaru Banju, Nagaokakyo (JP); Junko Watanabe, Nagaokakyo (JP); Takashi Kondo, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 19 days.

(21) Appl. No.: 16/283,859

(22) Filed: Feb. 25, 2019

(65) Prior Publication Data

US 2019/0185804 A1    Jun. 20, 2019

Related U.S. Application Data

(63) Continuation of application No. PCT/JP2017/044345, filed on Dec. 11, 2017.

(30) Foreign Application Priority Data

Dec. 20, 2016  (JP) .................................. 2016-247148

(51) Int. Cl.
*C12M 1/26* (2006.01)
*C12M 1/12* (2006.01)
(Continued)

(52) U.S. Cl.
CPC .............. *C12M 33/14* (2013.01); *B01D 39/10* (2013.01); *B01D 39/12* (2013.01); *B01D 39/20* (2013.01);
(Continued)

(58) Field of Classification Search
CPC ........ C12M 33/14; C12M 47/02; C12M 1/12; C12M 29/04; B01D 39/10; B01D 39/12;
(Continued)

(56) References Cited

U.S. PATENT DOCUMENTS

2002/0033367 A1   3/2002  Prince
2015/0087016 A1   3/2015  Takagi
(Continued)

FOREIGN PATENT DOCUMENTS

JP    2000501338 A    2/2000
JP    2015062400 A    4/2015
(Continued)

OTHER PUBLICATIONS

International Search Report issued for PCT/JP2017/044345, dated Jan. 16, 2018.
(Continued)

*Primary Examiner* — John Kim
(74) *Attorney, Agent, or Firm* — Arent Fox LLP (57) ABSTRACT

A cell filtration filter that includes a metal membrane part that has a first main surface on which the cells are to be captured and a second main surface that opposes the first main surface. The metal membrane part has a plurality of hole edges that define a plurality of first through holes and a support region that is arranged around the hole edges and supports the hole edges. In the support region of the metal membrane part, a plurality of second through holes, which have smaller openings than the first through holes, are arranged so as to surround the hole edges. On the first main surface of the membrane part, the hole edges are raised with respect to the support region.

20 Claims, 4 Drawing Sheets

(51) Int. Cl.
  *B01D 39/10* (2006.01)
  *B01D 39/12* (2006.01)
  *B01D 39/20* (2006.01)
  *B01D 69/06* (2006.01)
  *B01D 71/02* (2006.01)
  *C12M 1/00* (2006.01)

(52) U.S. Cl.
  CPC ......... *B01D 39/2027* (2013.01); *B01D 69/06* (2013.01); *B01D 71/022* (2013.01); *C12M 1/12* (2013.01); *C12M 29/04* (2013.01); *C12M 47/02* (2013.01); *B01D 2325/021* (2013.01); *B01D 2325/04* (2013.01)

(58) Field of Classification Search
  CPC .... B01D 39/20; B01D 39/2027; B01D 69/06; B01D 71/022; B01D 2325/04; B01D 2325/021
  See application file for complete search history.

(56) References Cited

U.S. PATENT DOCUMENTS

2016/0041075 A1   2/2016   Kamba
2016/0054223 A1   2/2016   Kamba

FOREIGN PATENT DOCUMENTS

| JP | 2015087382 A | 5/2015 |
| WO | 2014192917 A1 | 12/2014 |
| WO | 2016140183 A1 | 9/2016 |

OTHER PUBLICATIONS

Written Opinion of the International Searching Authority issued for PCT/JP2017/044345, dated Jan. 16, 2018.

CELL FILTRATION FILTER

CROSS REFERENCE TO RELATED APPLICATIONS

The present application is a continuation of International application No. PCT/JP2017/044345, filed Dec. 11, 2017, which claims priority to Japanese Patent Application No. 2016-247148, filed Dec. 20, 2016, the entire contents of each of which are incorporated herein by reference.

FIELD OF THE INVENTION

The present invention relates to a cell filtration filter for filtering cells.

BACKGROUND OF THE INVENTION

Cells of a desired size are required in medicinal efficacy investigations and so forth in which cells (cell aggregates (spheroids)) are used.

For example, Patent Document 1 discloses a technique in which cells are classified by filtering the cells using a filter.

Patent Document 1: Japanese Unexamined Patent Application Publication No. 2015-62400

SUMMARY OF THE INVENTION

In recent years, it has been desired to obtain cells of a specified size with higher precision when filtering cells using a filter. As described herein, the inventors of the present application discovered a new issue in that, when a liquid passes through the through holes of a filter together with cells when performing filtration, cells that were initially captured by the filter deform as they are moved toward the through holes by the flow of the liquid and cells having a greater size than the through holes end up passing through the through holes.

An object of the present invention is to provide a cell filtration filter that can improve the precision of cell filtration for obtaining cells of a desired size. In particular, an object of the present invention is to provide a cell filtration filter that suppresses a situation in which, when a liquid passes through the through holes of the filter together with cells when performing filtration of cells using the filter, cells that were initially captured by the filter deform as the cells are moved toward the through holes by the flow of the liquid and cells having a greater size than the through holes end up passing through the through holes.

A cell filtration filter of an aspect of the present invention includes a metal membrane part that has a first main surface on which the cells are to be captured and a second main surface that faces the first main surface. The metal membrane part has a plurality of hole edges that define a plurality of first through holes and a support region that is arranged around the hole edges and supports the hole edges. In the support region of the membrane part, a plurality of second through holes, which have smaller openings than the first through holes, are arranged so as to surround the hole edges. On the first main surface of the membrane part, the hole edges are raised with respect to the support region.

According to the present invention, there can be provided a cell filtration filter that can improve the precision of cell filtration for obtaining cells of a desired size.

DETAILED DESCRIPTION OF THE PREFERRED EMBODIMENTS (Circumstances Leading to Present Invention and Knowledge Forming Basis of Present Invention)

Cell aggregates are used as models of cancer cells when investigating medicinal efficacy with respect to cancer. Cancer cells have different sizes depending on the degree of progression of the cancer. In addition, when the sizes of cancer cells differ, the drugs that exhibit an effect are also different. For example, a drug that is effective on early-stage cancers or small cancer tissues may be less effective on advanced cancers or large cancer tissues. Therefore, in medicinal efficacy investigations using cell aggregates, variations occur in medicinal efficacy data when the medicinal efficacy investigations are performed using cell aggregates having different dimensions. Therefore, it is critical that cell aggregates having uniform dimensions be obtained in order to suppress such variations in medicinal efficacy data.

Furthermore, cell aggregates are used as regenerative medicine tissues. Tissues of a desired size are required in this case, and it is difficult to manufacture tissues of a desired size using methods for manufacturing cell aggregates, and it is more efficient to manufacture cell aggregates of various sizes and then choose the tissues having a desired size. Therefore, it is required to choose desired tissues with high precision.

Furthermore, not only in the case of cell aggregates, there is also a demand to improve classification precision when classifying cells into cells of a desired size by performing filter filtration for a specific intended purpose such as medicinal efficacy investigations.

The inventors of the present application diligently investigated filtration of cells using filters and discovered a new issue as a factor that impedes cells of a desired size from being obtained. This new issue will be described below.

Figure 5:
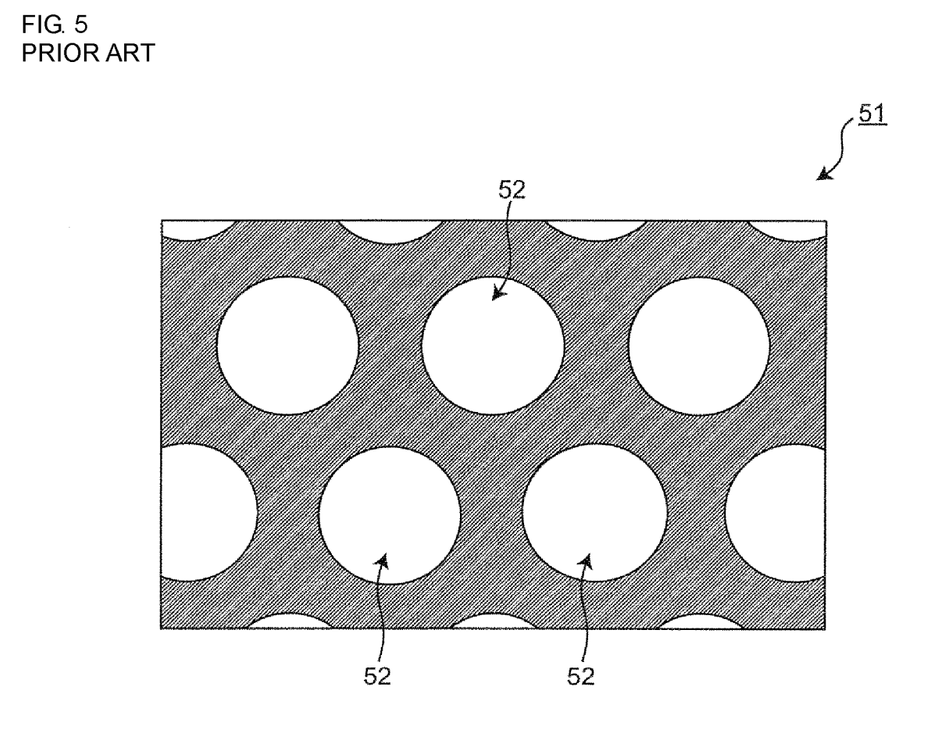
FIG. 5 is a partial enlarged plan view of a cell filtration filter according to a comparative example of the present invention.
Figure 6A:
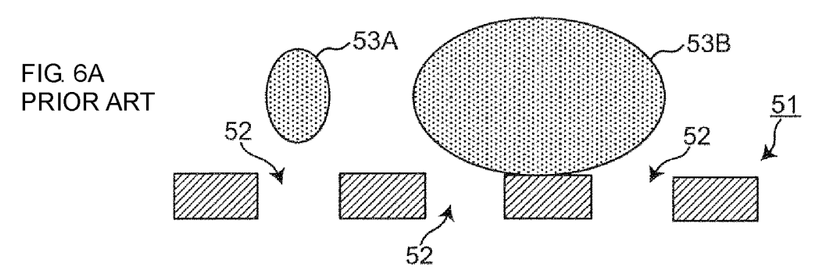
FIGS. 6A to 6C are sectional views of the cell filtration filter in FIG. 5 illustrating cell filtration states.

Let us consider a case in which cell aggregates of various sizes are manufactured and then filtration is performed using a filter such that cell aggregates having a size greater than the desired size are captured by the filter and cell aggregates that are smaller than or equal to the desired size pass through the filter and are recovered. In this case, filtration is performed using a filter provided with a plurality of through holes (mesh holes) of the same size, which size is set depending on the size of the cell aggregates desired to be captured. Here, cell filtration using a filter of a comparative example of the present invention considered by the inventors will be described using the schematic drawings of FIGS. 5 and 6A to 6C. FIG. 5 is a partial enlarged plan view of a cell filtration filter 51 (hereafter, filter 51) according to a comparative example of the present invention, and FIGS. 6A to 6C are schematic sectional views of the filter 51 illustrating cell filtration states.

As illustrated in FIG. 5, a plurality of circular through holes 52 of the same size are formed in the filter 51 of the comparative example. As illustrated in FIG. 6A, a liquid containing cell aggregates is supplied to an upstream side of the filter 51. A cell aggregate 53A having a smaller size than the through holes 52 of the filter 51 passes through a through hole 52 of the filter 51 together with the liquid and moves downstream from the filter 51. In contrast, a cell aggregate 53B having a larger size than the through holes 52 of the filter 51 cannot pass through the through holes 52 and is captured on the upstream-side surface of the filter 51.

Figure 6B:
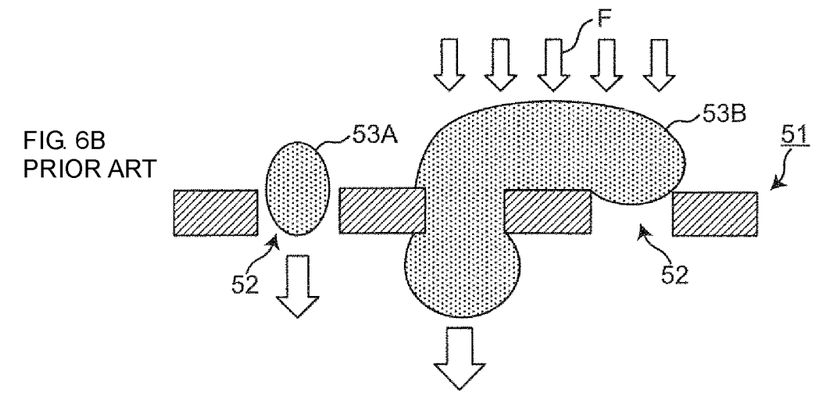
Figure 6C:
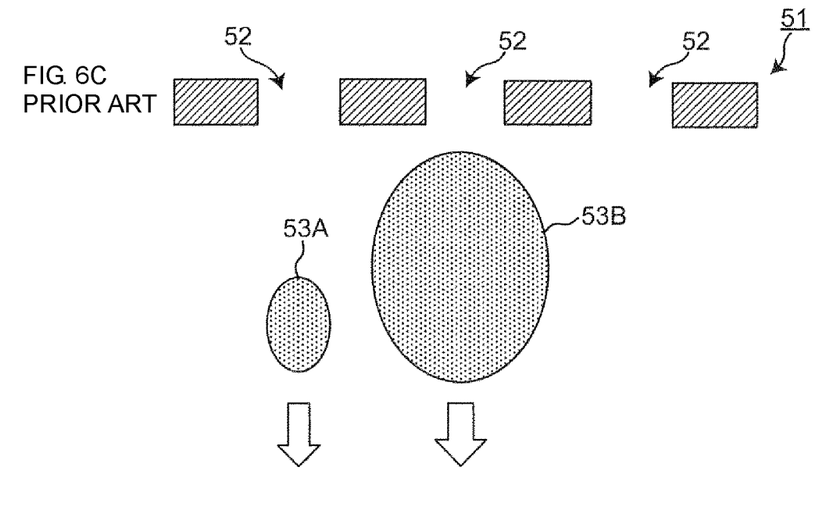

However, as illustrated in FIG. 6B, a liquid flow F that passes through the through holes 52 of the filter 51 is generated when filtration is performed, and the liquid passes through the through holes 52 and moves downstream from the filter 51. Consequently, the cell aggregate 53B that was initially captured by the filter 51 is pulled toward a through hole 52 and deformed by the liquid flow F. As a result, as illustrated in FIG. 6C, a leak may occur in which the cell aggregate 53B having a larger size than the through holes 52 of the filter 51 deforms and ends up passes through a through hole 52. In other words, since the cell aggregates and the liquid simultaneously flow into the through holes 52 of the filter 51, a cell aggregate may be pulled and deformed by this liquid flow and a cell aggregate having a greater size than the through holes 52 may end up passing through a through hole 52.

In order to obtain cells (also cell aggregates) of a desired size using filter filtration, it is important to optimize the size of the through holes of the filter. However, since the appropriate size of the through holes will differ depending on how the liquid containing cells is made to flow and the concentration of cells and so forth within the liquid, optimization of the size of the through holes is not a simple matter.

Thus, the inventors of the present application discovered a new issue in that, when a liquid passes through the through holes of a filter together with cells when performing filtration of cells using a filter, cells that were initially captured by the filter deform as the cells are moved toward the through holes by the flow of the liquid and cells having a greater size than the through holes end up passing through the through holes, and the inventors made the present invention in order to solve this issue.

A cell filtration filter of an aspect of the present invention includes a metal membrane part that has a first main surface on which the cells are to be captured and a second main surface that faces the first main surface. The metal membrane part has a plurality of hole edges that define a plurality of first through holes and a support region that is arranged around the hole edges and supports the hole edges. In the support region of the membrane part, a plurality of second through holes, which have smaller openings than the first through holes, are arranged so as to surround the hole edges that define the plurality of first through holes. On the first main surface of the membrane part, the hole edges that define the plurality of first through holes are raised with respect to the support region.

With this configuration, a cell filtration filter is realized that can improve the precision of cell filtration for obtaining cells of a desired size.

In the cell filtration filter, the second main surface of the membrane part may be flat. With this configuration, a situation in which cells that have passed through the first through holes and adhere to the second main surface can be suppressed.

In the cell filtration filter, the second through holes may be polygonal holes. With this configuration, an opening ratio is more easily secured. In addition, the meaning of "polygonal" is not limited to the case where the lines connecting vertexes are straight lines and also includes the case where the lines connecting vertexes are curved lines. When curved lines are used to connect the vertexes, it is easier to provide the second through holes in the support region and the opening ratio can be increased.

In the cell filtration filter, the second through holes may be arranged in a lattice pattern in the support region. With this configuration, a larger number of second through holes can be efficiently arranged, and the opening ratio is more easily secured.

In the cell filtration filter, the first through holes may be circular holes. With this configuration, the size of cells that pass through the first through holes is more easily controlled.

In the cell filtration filter, a major axis of each second through hole may be smaller than a major axis of each first through hole, and an interval between adjacent second through holes may be smaller than an interval between adjacent first through holes. With this configuration, the opening ratio of the cell filtration filter can be increased.

The area of a liquid that passes through the cell filtration filter can be increased by increasing the opening ratio of the cell filtration filter in this way. Therefore, an effect of increasing the flow rate of the liquid and reducing pressure loss can be obtained.

Hereafter, an embodiment of the present invention will be described in detail on the basis of the drawings. In addition, in each drawing, each element is illustrated in an exaggerated manner in order to simplify the explanation.

Embodiment

Figure 1:
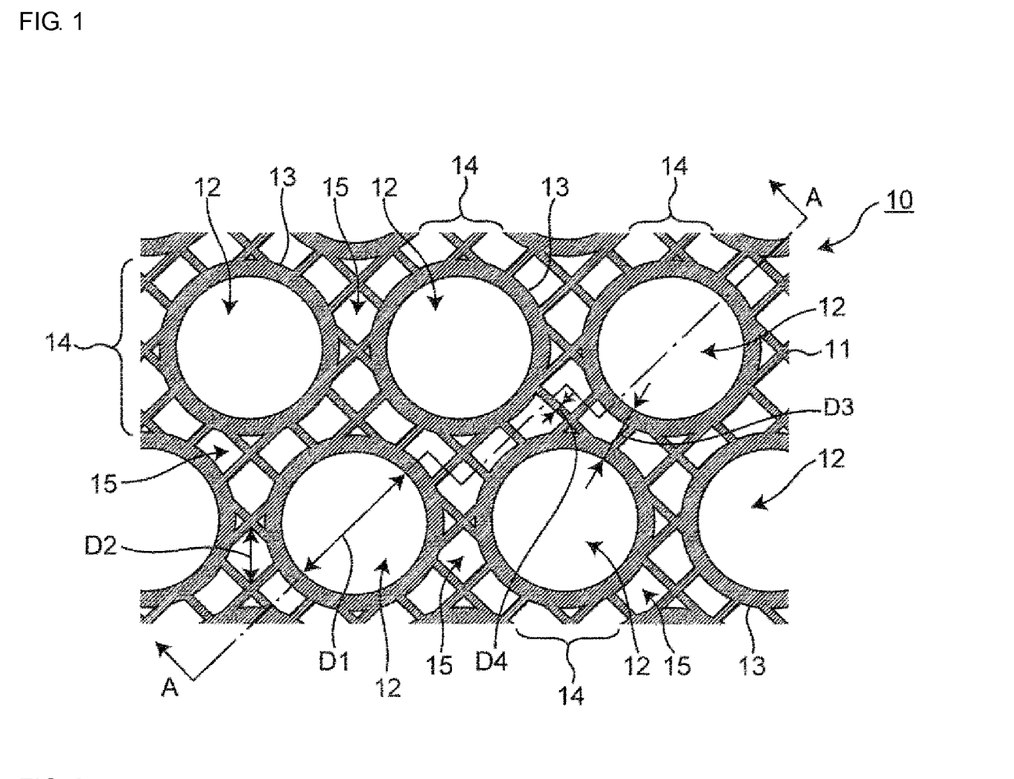
FIG. 1 is a partial enlarged plan view of a cell filtration filter according to an embodiment of the present invention.

FIG. 1 illustrates a partial enlarged plan view of a cell filtration filter 10 according to an embodiment of the present invention. In addition, FIG. 2 illustrates a sectional view of the cell filtration filter 10 taken along line A-A in FIG. 1.

Figure 2:
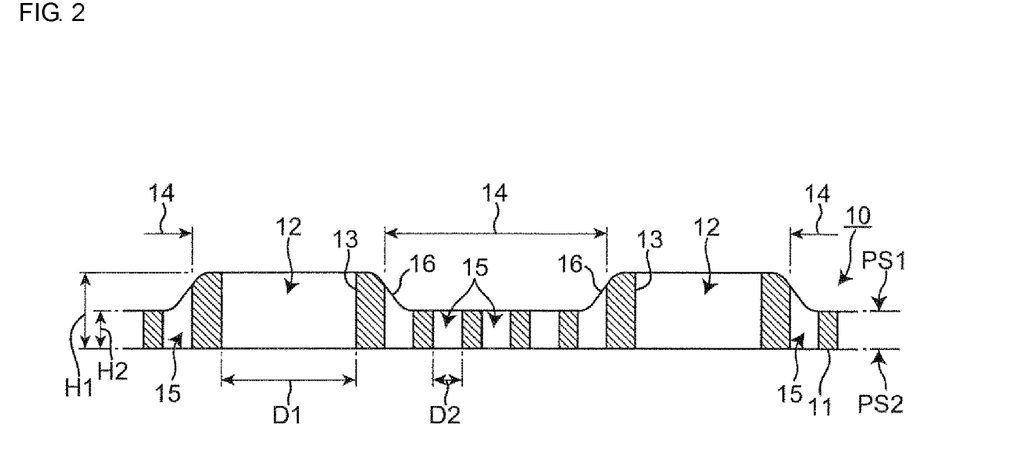
FIG. 2 is a sectional view of the cell filtration filter in FIG. 1 taken along line A-A.

As illustrated in FIGS. 1 and 2, the cell filtration filter 10 includes a membrane part 11 that has a first main surface PS1 and a second main surface PS2, which face each other, and that has a plurality of first through holes 12 that penetrate between the two main surfaces. The cell filtration filter 10 is a plate-like structure in which the plurality of first through holes 12 are provided at a constant interval across the membrane part 11, for example. For example, the cell filtration filter 10 is a perforated metal membrane for obtaining (filtering/classifying) cells of a desired size by allowing a liquid containing a plurality of cells of different sizes to pass therethrough.

In the present specification, "cell aggregate" is also included in the meaning of "cell", and "cell aggregate" refers to an agglomeration of cells formed when a plurality of cells stick together. "Cell aggregate" can be formed using cancer cells, stem cells, iPS cells, and so forth, for example.

The entirety of the cell filtration filter 10 is not illustrated in FIGS. 1 and 2, but in this embodiment, the cell filtration filter 10 includes a metal mesh having a circular outer shape, for example. The dimensions of the cell filtration filter 10 are a diameter of 7.8 mm and a thickness of 20 μm. The material constituting the cell filtration filter 10 is a metal material, and this metal material may be gold, silver, copper, platinum, nickel, stainless steel, titanium, palladium, or an alloy of any of these metals, for example. Gold, nickel, stainless steel, and titanium are particularly preferred as the material of the cell filtration filter 10 from the viewpoint of biocompatibility with cells. The cell filtration filter 10 is not limited to having a circular outer shape, and the cell filtration filter 10 may instead have an outer shape in the form of a rectangular shape such as an oblong, a square, or the like, or an ellipse, for example.

As illustrated in FIG. 1, the membrane part 11 of the cell filtration filter 10 includes a plurality of hole edges 13 that define the plurality of first through holes 12 and a support region 14 that is arranged around the hole edges 13 and supports the hole edges 13. The first through holes 12 are circular holes and the hole edges 13 are annular parts arranged so as to surround the circular holes. The individual first through holes 12 have the same shape and size as each other, and are arranged so as to be uniformly distributed across the membrane part 11. The first through holes 12 are not limited to being circular holes, and may instead have a rectangular shape such as an oblong, square, or the like, or an ellipse or the like, for example. Furthermore, the hole edges 13 surround the peripheries of the first through holes 12, and have shapes that correspond to the shapes of the first through holes 12.

The support region 14 is an integrated region of the membrane part 11 that is connected to each of the hole edges 13 and extends between the individual hole edges 13. As illustrated in FIG. 1, a plurality of second through holes 15 that have smaller openings than the first through holes 12 are arranged in the support region 14 of the membrane part 11 so as to surround the individual hole edges 13. The second through holes 15 consist of holes having a plurality of different polygonal shapes having different numbers of vertexes (for example, quadrilateral holes and triangular holes) mixed together. The second through holes 15 are not limited to being holes having polygonal shapes such as squares, rectangles, triangles, and so on, and for example, may instead be holes having a circular shape, an elliptical shape, or the like. In this embodiment, quadrilateral holes and polygonal holes (for example, triangular holes) formed of parts of quadrilateral holes are arranged as the second through holes 15 in the support region 14 by projecting a plurality of quadrilateral holes arranged in a lattice pattern onto the membrane part 11 and removing the regions corresponding to the first through holes 12 and the hole edges 13. The second through holes 15 are not limited to being arranged in only a lattice pattern, and for example, may instead be arranged in an irregular manner. In the case where the first through holes 12 have a circular shape as in FIG. 1, it is possible to arrange a greater number of holes when holes having a plurality of different shapes are mixed together as the second through holes 15 arranged around the first through holes 12, and the opening ratio in the support region 14 can be increased.

In the membrane part 11, a major axis D1 of the first through holes 12 is set so as to be smaller than the size of the cells that are desired to be captured by the membrane part 11, and a major axis D2 of the second through holes 15 is smaller than the major axis D1 of the first through holes 12. In addition, an interval D4 between adjacent second through holes 15 is set so as to be smaller than an interval D3 between adjacent first through holes 12. In this specification, in a two-dimensional observation image obtained when cells are arranged in a liquid and observed using a microscope, the longest line among lines that connect any two points on the outer periphery of a cell is taken as the length of the cell and the average value of the lengths of at least three cells that are of a size that is to be captured is taken as the size of the cells. In addition, in this specification, the line corresponding to the longest length among lines connecting any two points on the outer periphery of a through hole is taken to be the major axis of the through hole. Furthermore, in this specification, the shortest line segment among line segments connecting the outer peripheries of adjacent through holes is taken to be the interval between adjacent through holes. In this embodiment, for example, the size of cells that are to be captured is 500 µm, the major axis D1 of the first through holes 12 is 100 µm, and the major axis D2 of the second through holes 15 is 20 µm. In addition, the interval D3 between adjacent first through holes 12 is 30 µm, and the interval D4 between adjacent second through holes 15 is 5 µm.

As illustrated in FIG. 2, the hole edges 13 are raised with respect to the support region 14 on the first main surface PS1 of the membrane part 11. In other words, on the first main surface PS1, the edges of the openings of the first through holes 12 protrude outwardly in the thickness direction relative to the edges of the openings of the second through holes 15 in the support region 14. In addition, as illustrated in FIG. 2, on the first main surface PS1, the hole edges 13 and the support region 14, which have different heights from each other, are connected to each other by inclined surfaces 16. In contrast, the second main surface PS2 of the membrane part 11 is formed so as to be a flat surface (planar surface). In FIG. 2, the relationship H1>H2 is illustrated, where H1 is the height of the hole edges 13 and H2 is the height of the support region 14 relative to the second main surface PS2. In addition, in this specification, the statement that the second main surface PS2 of the membrane part 11 is "flat" means that an arithmetic mean roughness of the second main surface PS2 is less than or equal to 0.7 µm. Measurement of the arithmetic mean roughness was performed using a probe-type surface profilometer DEKTAK 150 (Registered Trademark) manufactured by ULVAC Inc., and the arithmetic mean roughness was taken to be the average value of values measured at five locations across the second main surface PS2.

Next, an example of a method of manufacturing the cell filtration filter 10 of this embodiment will be described. FIGS. 3A to 3G are partial sectional views illustrating an example of a method of manufacturing the cell filtration filter 10, and illustrate a part of the cell filtration filter 10 that includes a first through hole 12 and the surrounding support region 14.

Figure 3A:
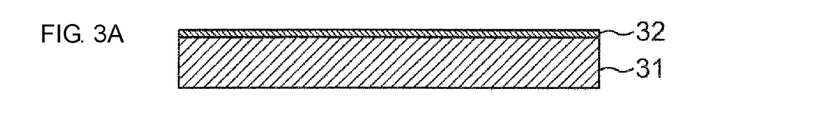
FIGS. 3A to 3G are diagrams illustrating a method of manufacturing a cell filtration filter according to an embodiment.

As illustrated in FIG. 3A, a Cu thin film 32 is formed on a substrate 31 composed of silicon or the like. The Cu thin film 32 can be formed using vapor deposition or sputtering, for example. Better surface film quality can be obtained when the Cu thin film 32 is formed using sputtering compared with when the CU thin film 32 is formed using vapor deposition.

Figure 3B:
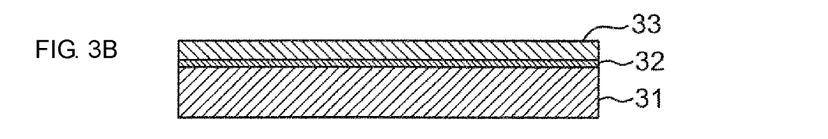

Next, as illustrated in FIG. 3B, a resist film 33 is formed on the Cu thin film 32. Specifically, the resist film 33 is formed by applying a resist onto the Cu thin film 32 using spin coating for example, and then performing a drying treatment. The resist film 33 is formed to have a thickness of around 2 µm, for example.

Figure 3C:
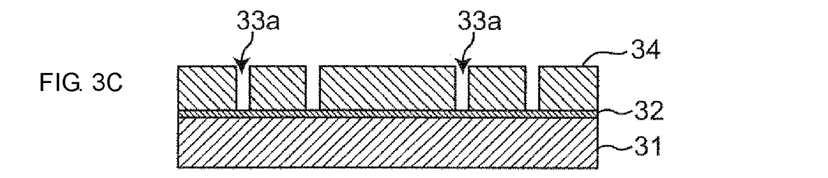

Next, as illustrated in FIG. 3C, the resist film 33 is subjected to a light exposure/development treatment (first light exposure/development treatment) and parts corresponding to the membrane part 11 are removed from the resist film 33, and as a result a first resist image 34 having grooves 33a is formed.

Figure 3D:
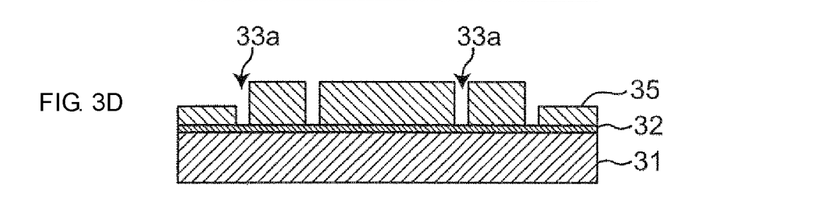

Next, as illustrated in FIG. 3D, the first resist image 34 is subjected to another light exposure/development treatment (second light exposure/development treatment), parts corresponding to the support region 14 of the membrane part 11 are partially removed from the first resist image 34 and the resist film height is reduced. Thus, a second resist image 35 is formed in which the resist film height in the parts corresponding to the support region 14 is reduced compared with the other parts.

For example, the resist film height can be reduced in some parts by using a mask filter or the like to provide parts where the first resist image 34 is exposed to light and parts where the first resist image 34 is not exposed to light. In addition, for example, parts where the resist film height changes in an inclined manner (for example, parts corresponding to parts where the inclined surfaces 16 (refer to FIG. 2) that connect the hole edges 13 and the support region 14 to each other in the membrane part 11 are formed) can be formed by providing a difference in light exposure time within the parts exposed to light.

Figure 3E:
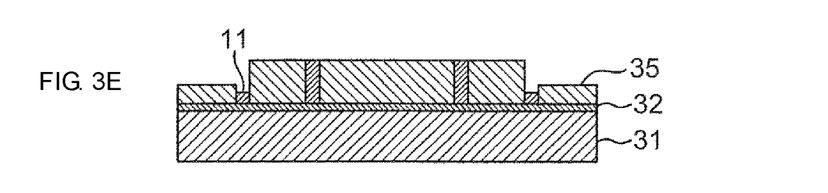

Next, as illustrated in FIG. 3E, a metal film, i.e., the membrane part 11 is formed in the grooves 33a of the second resist image 35. For example, the membrane part 11 is formed using an electroplating method. Since the resist film heights are different in different parts of the second resist image 35, the depths of the grooves 33a are also different in these parts of the second resist image 35. Therefore, for example, the growth of plating may be suppressed for shallow grooves 33a by arranging a baffle plate above the grooves 33a. As a result, as illustrated in FIG. 3E, a membrane part 11 having heights that correspond to the depths of the individual grooves 33a is formed.

Figure 3F:
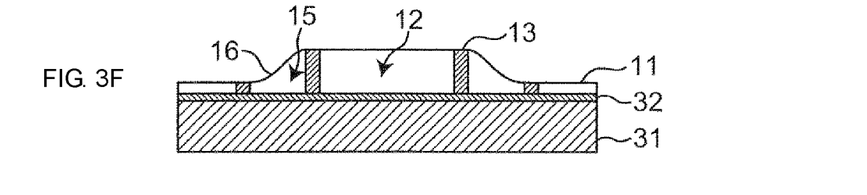
Figure 3G:
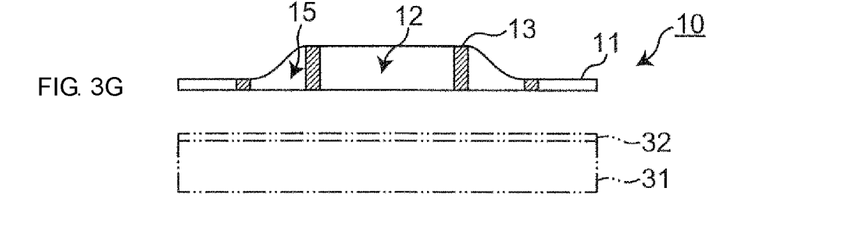

Next, as illustrated in FIG. 3F, dipping in a solvent (such as acetone) is performed and the second resist image 35 is dissolved and removed from the Cu thin film 32. After that, as illustrated in FIG. 3G, the Cu thin film 32 and the substrate 31 are subjected to a dissolving treatment, and thus, manufacture of the cell filtration filter 10 having the first through holes 12 and the second through holes 15 and in which the hole edges 13, which define the first through holes 12, are raised is complete. The manufacturing method described using FIGS. 3A to 3G is an example, and another manufacturing method may instead be employed.

A case in which a cell filtration process is performed using the cell filtration filter 10 of this embodiment will be described using a partial sectional view of the cell filtration filter 10 illustrated in FIG. 4.

Figure 4:
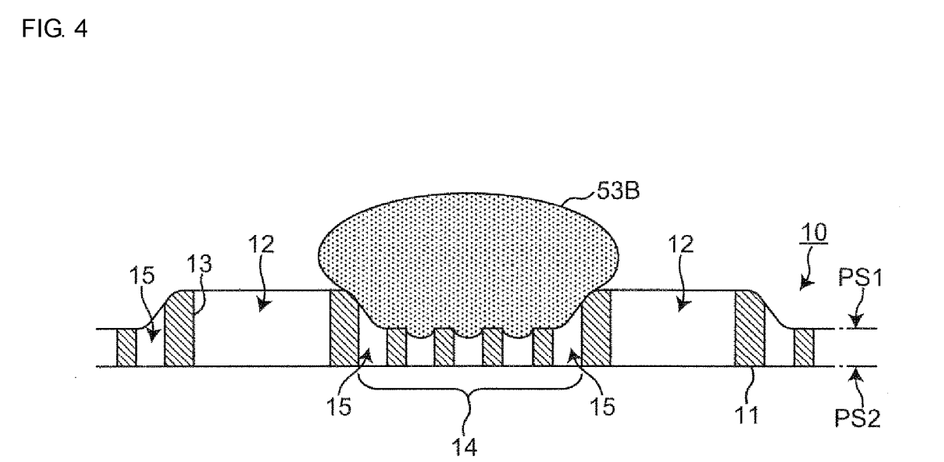
FIG. 4 is a diagram illustrating the state of a process of filtering cells in a cell filtration filter according to an embodiment.

As illustrated in FIG. 4, a liquid containing cells is supplied to the upstream side (first main surface PS1 side) the membrane part 11 of the cell filtration filter 10. Cells having a smaller size than the first through holes 12 of the cell filtration filter 10 pass through the first through holes 12 together with the liquid and move toward the downstream side (second main surface PS2 side). On the other hand, a cell 53B having a larger size than the first through holes 12 is not able to pass through the first through holes 12 (and the second through holes 15) and is captured on the first main surface PS1, which is on the upstream side of the membrane part 11.

In the cell filtration filter 10 of this embodiment, a plurality of second through holes 15 having the major axis D2 that is smaller than the major axis D1 of the first through holes 12 are formed in the support region 14 surrounding the first through holes 12. As a result, the liquid supplied from the upstream side of the membrane part 11 is not concentrated at only the first through holes 12 and instead passes through the surrounding second through holes 15 and moves toward the downstream side. Therefore, the flow of liquid through the membrane part 11 is not concentrated at only the first through holes 12 and can also be dispersed to the second through holes 15. Therefore, a situation in which a cell 53B captured by the cell filtration filter 10 is pulled toward a first through hole 12 and deformed by the flow of the liquid is suppressed.

Furthermore, in the cell filtration filter 10, the hole edges 13, which define the first through holes 12, are raised relative to the surrounding support region 14. Therefore, as illustrated in FIG. 4, a situation in which a cell 53B captured in the support region 14 climbs over the hole edge 13 and moves into the inside of the first through hole 12 can be suppressed.

Consequently, the generation of a "leak" in which a cell 53B having a larger size than the first through holes 12 is deformed by the flow of the liquid and ends up passing through a first through hole 12 can be suppressed. Therefore, the precision of cell filtration can be improved in the cell filtration filter 10.

In addition, on the first main surface PS1 of the cell filtration filter 10, the inclined surfaces 16 are provided between the raised hole edges 13 and the support region 14. As a result, corner portions located between the hole edges 13 and the support region 14 can be given a smooth shape, and an issue in which a cell aggregate breaks up as a result of colliding with such a corner portion and ends up passing through a first through hole 12 is unlikely to occur.

Furthermore, the second main surface PS2 of the cell filtration filter 10 is formed as a flat surface. In this way, it can be ensured that cells are unlikely to adhere to the second peripheral surface PS2 after passing through the first through holes 12.

Furthermore, in addition to the first through holes 12 the size of the major axis D1 of which is set on the basis of the cells that are the targets of filtration, the cell filtration filter 10 is provided with the second through holes 15 that have the major axis D2 that is smaller than the major axis D1 of the first through holes 12. Therefore, the opening ratio of the cell filtration filter 10 can be adjusted by altering the size of the major axis D2 of the second through holes 15 or the number of second through holes 15. Therefore, the opening ratio of the cell filtration filter 10 can be easily set, the degree of freedom of design with respect to the arrangement interval and number of first through holes 12 is increased, and cell filtration filters having a variety of required specifications can be provided.

In addition, in the cell filtration filter 10, the interval D4 between adjacent second through holes 15 is set to be smaller than the interval D3 between adjacent first through holes 12. Thus, the opening ratio of the support region 14 can be increased and the opening ratio of the cell filtration filter 10 can be increased.

In the above-described embodiment, an example is described in which the first through holes 12 are circular holes and the second through holes 15 consist of a plurality of different polygonal holes that form a square lattice arrangement of holes, but the present invention is not limited to this combination. As described above, the first through holes and the second through holes may have various shapes. For example, compared with the case where the first through holes have a square shape, it is easier to control the size of cells that can pass through the cell filtration filter in the case where the first through holes are circular holes. In addition, compared with a case where a plurality of circular holes are arranged in a distributed manner as the second through holes, it is easier to secure a large opening ratio when the second through holes consist of holes having a plurality of different polygonal shapes forming a square lattice arrangement of holes. Furthermore, although it is preferable for the second through holes, the main purpose of which is to allow the liquid to pass therethrough, to be arranged so as to be substantially uniformly distributed over the entire support region, depending on the arrangement relationship of the second through holes with respect to the first through holes, variations may be provided in the arrangement density of the second through holes such as in the center or at the periphery of the support region.

Although the present invention has been sufficiently described in relation to a preferred embodiment while referring to the accompanying drawings, various modifications and amendments will be evident to people skilled in the art. So long as such modifications and amendments do not depart from the scope of present invention as defined by the appended claims, such modifications and amendments are to be understood as being included in the scope of the present invention.

The cell filtration filter of the present invention is capable of improving the precision of cell filtration for obtaining cells of a desired size, and therefore for example, the cell filtration filter is useful in application to fields such as medicinal efficacy investigation and manufacture of regenerative medical treatments.

REFERENCE SIGNS LIST 10 cell filtration filter
11 membrane part
12 first through hole
13 hole edge
14 support region
15 second through hole
16 inclined surface
31 substrate
32 Cu thin film
33 resist film
33a groove
34 first resist image
35 second resist image
53B cell
PS1 first main surface
PS2 second main surface
D1 major axis of first through hole
D2 major axis of second through hole
D3 interval between adjacent first through holes
D4 interval between adjacent second through holes

The invention claimed is:

1. A cell filtration filter comprising:
a metal membrane part that has a first main surface and a second main surface opposing the first main surface, the metal membrane part having a plurality of hole edges that each respectively define a plurality of first through holes and a support region arranged around the hole edges and supporting the hole edges,
wherein the support region of the metal membrane part includes a plurality of second through holes, each of the plurality of second through holes arranged so as to surround the hole edges and having smaller openings than the first through holes, and
wherein, on the first main surface of the metal membrane part, the hole edges are raised with respect to the support region.

2. The cell filtration filter according to claim 1, wherein the second main surface of the metal membrane part is flat.

3. The cell filtration filter according to claim 2, wherein the plurality of second through holes have a polygonal shape.

4. The cell filtration filter according to claim 3, wherein the plurality of second through holes are arranged in a lattice pattern in the support region.

5. The cell filtration filter according to claim 4, wherein the first through holes have a circular shape.

6. The cell filtration filter according to claim 5, wherein a first major axis of the plurality of second through holes is smaller than a second major axis of the plurality of first through holes, and a first interval between adjacent second through holes of the plurality of second through holes is smaller than a second interval between adjacent first through holes of the plurality of first through holes.

7. The cell filtration filter according to claim 1, wherein the plurality of second through holes have a polygonal shape.

8. The cell filtration filter according to claim 7, wherein the plurality of second through holes are arranged in a lattice pattern in the support region.

9. The cell filtration filter according to claim 8, wherein the first through holes have a circular shape.

10. The cell filtration filter according to claim 9, wherein a first major axis of the plurality of second through holes is smaller than a second major axis of the plurality of first through holes, and a first interval between adjacent second through holes of the plurality of second through holes is smaller than a second interval between adjacent first through holes of the plurality of first through holes.

11. The cell filtration filter according to claim 1, wherein the plurality of second through holes are arranged in a lattice pattern in the support region.

12. The cell filtration filter according to claim 11, wherein the first through holes have a circular shape.

13. The cell filtration filter according to claim 12, wherein a first major axis of the plurality of second through holes is smaller than a second major axis of the plurality of first through holes, and a first interval between adjacent second through holes of the plurality of second through holes is smaller than a second interval between adjacent first through holes of the plurality of first through holes.

14. The cell filtration filter according to claim 1, wherein the first through holes have a circular shape.

15. The cell filtration filter according to claim 14, wherein a first major axis of the plurality of second through holes is smaller than a second major axis of the plurality of first through holes, and a first interval between adjacent second through holes of the plurality of second through holes is smaller than a second interval between adjacent first through holes of the plurality of first through holes.

16. The cell filtration filter according to claim 1, wherein a first major axis of the plurality of second through holes is smaller than a second major axis of the plurality of first through holes, and a first interval between adjacent second through holes of the plurality of second through holes is smaller than a second interval between adjacent first through holes of the plurality of first through holes.

17. The cell filtration filter according to claim 1, wherein a first major axis of the plurality of second through holes is smaller than a second major axis of the plurality of first through holes.

18. The cell filtration filter according to claim 1, wherein a first interval between adjacent second through holes of the plurality of second through holes is smaller than a second interval between adjacent first through holes of the plurality of first through holes.

19. The cell filtration filter according to claim 1, wherein a material of the metal membrane part is selected from gold, silver, copper, platinum, nickel, stainless steel, titanium, palladium, or an alloy thereof.

20. The cell filtration filter according to claim 1, wherein the plurality of second through holes have a plurality of different polygonal shapes having different numbers of vertexes.

\* \* \* \* \*